United States Patent [19]

Rhinehart et al.

[11] Patent Number: 4,919,146
[45] Date of Patent: Apr. 24, 1990

[54] BIOPSY DEVICE

[75] Inventors: Edward Rhinehart, Monroeville; James E. Machek, Bradfordwoods; Michael W. Sanctis, Pittsburgh, all of Pa.

[73] Assignee: Medrad, Inc., Pittsburgh, Pa.

[21] Appl. No.: 261,746

[22] Filed: Oct. 25, 1988

[51] Int. Cl.⁵ .............................................. A61B 10/00
[52] U.S. Cl. .................................... 128/752; 128/753; 128/759; 128/755; 604/27; 604/51; 604/164; 604/187; 604/218
[58] Field of Search ............. 128/305.1, 749, 751–755, 128/757, 758, 760, 763, 765; 604/22, 27, 51, 164, 181, 187, 188, 218, 222, 228, 240

[56] References Cited

U.S. PATENT DOCUMENTS

| | | | |
|---|---|---|---|
| 1,867,624 | 7/1932 | Hoffman | 128/754 |
| 2,850,007 | 9/1958 | Lingley | 128/754 |
| 3,749,085 | 7/1973 | Willson et al. | 128/305 |
| 3,837,345 | 9/1974 | Matar | 128/305 |
| 4,177,797 | 12/1979 | Baylis et al. | 128/754 |
| 4,461,305 | 7/1984 | Cibley | 128/754 |
| 4,542,749 | 9/1985 | Caselgrandi et al. | 128/752 |

FOREIGN PATENT DOCUMENTS 1268153 6/1983 U.S.S.R. .

Primary Examiner—Max Hindenburg
Assistant Examiner—Randy Shay
Attorney, Agent, or Firm—Fleit, Jacobson, Cohn, Price, Holman & Stern

[57] ABSTRACT

A biopsy device utilizes three components: a housing having an attached cannula, a drill bit/plunger component which is mounted in the housing so that the drill bit portion, having a cutting tip, extends through the cannula, the plunger snugly fitting within the housing, and a rotational energy element which couples with the drill bit/plunger component to enable the impartation of rotational motion to the cutting tip. Both drilling and aspirating action are utilized to retrieve a biopsy sample. In operation, the tissue to be sampled is punctured by a biopsy needle, the cannula of which is connected to the biopsy device. Thereafter, rotational energy is imparted to the drill bit/plunger component, causing tissue to be accumulated on the cutting tip. Once a sufficient amount of tissue has been accumulated, the rotational energy element and plunger/drill bit component are displaced in a proximal direction from the housing to cause the sample to be aspirated into the cannula syringe. The biopsy device is withdrawn from the tissue, and the sample is retrieved by exerting longitudinal pressure in a distal direction on the rotational energy element and, in turn, the drill bit/plunger component.

25 Claims, 3 Drawing Sheets

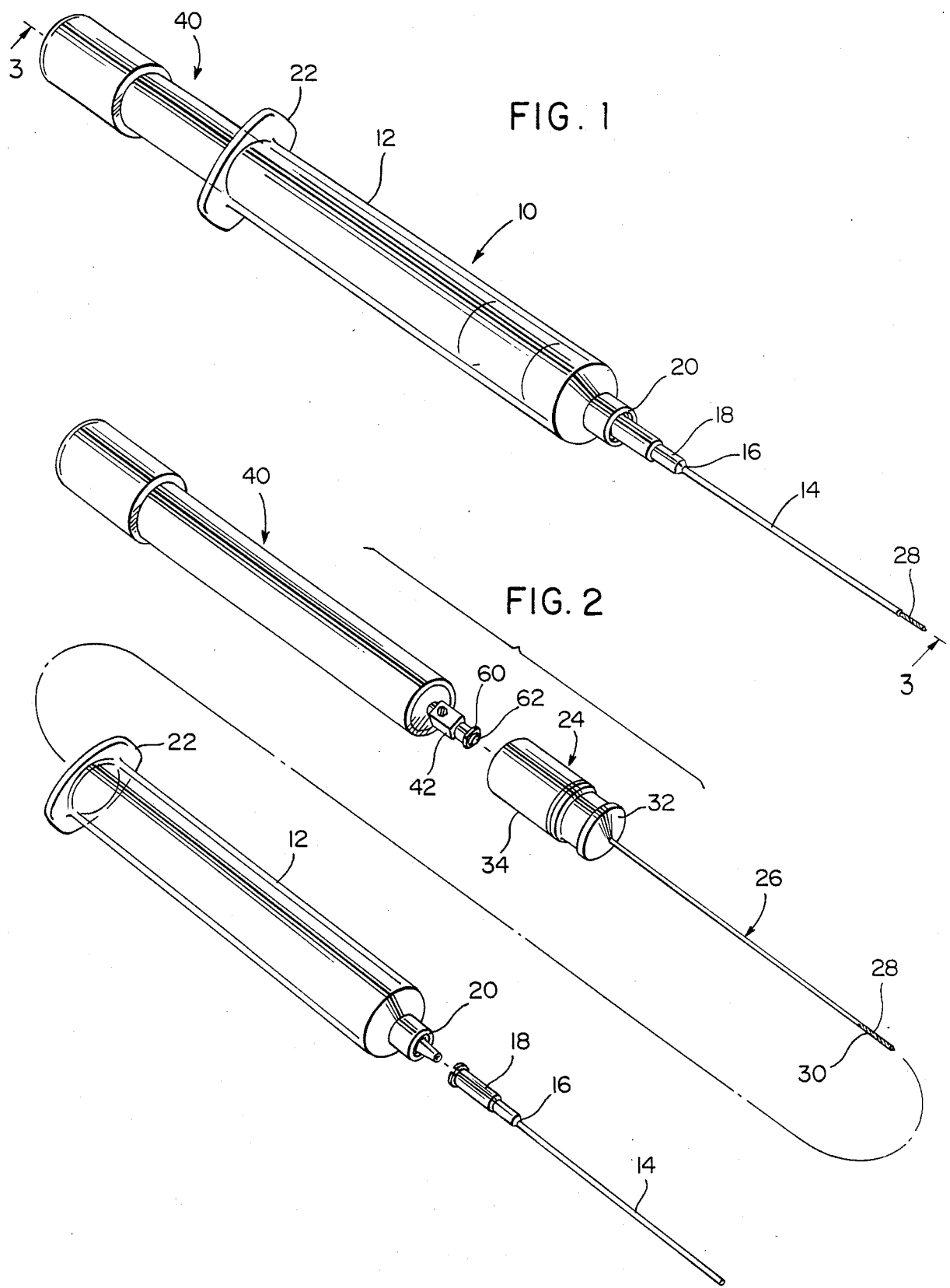

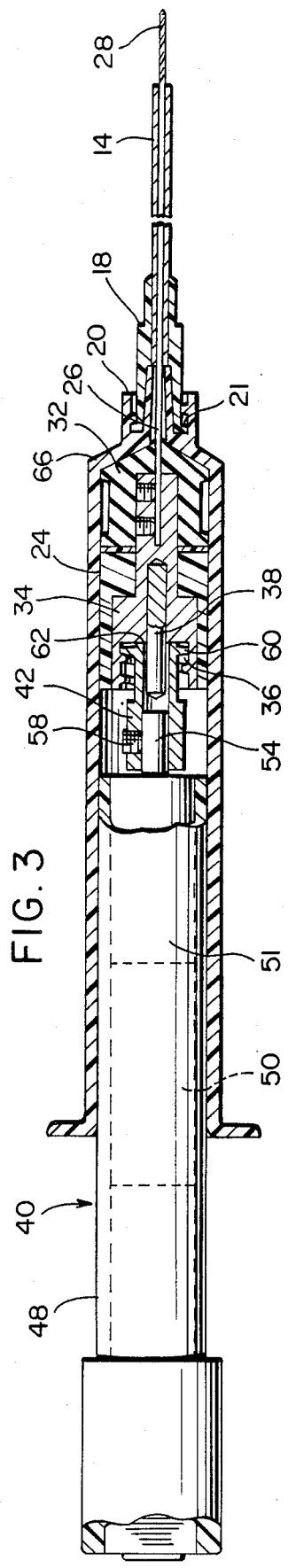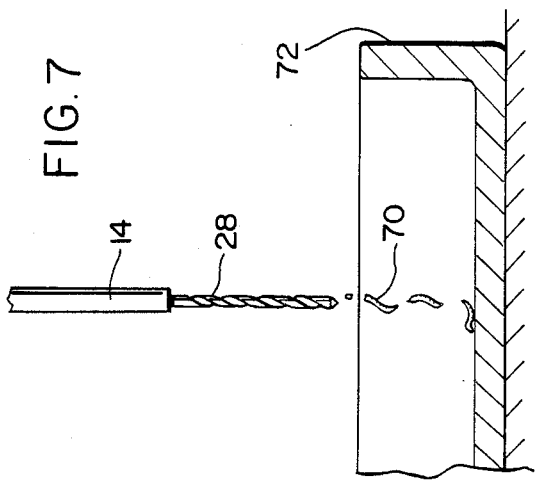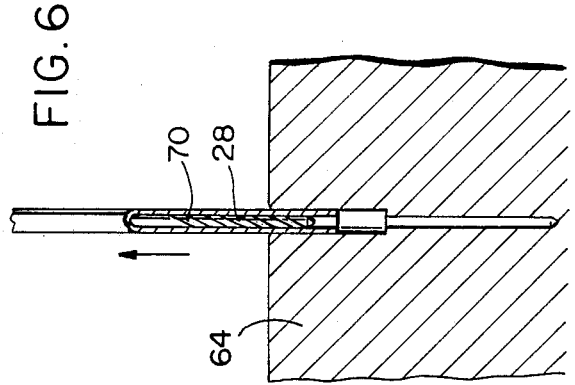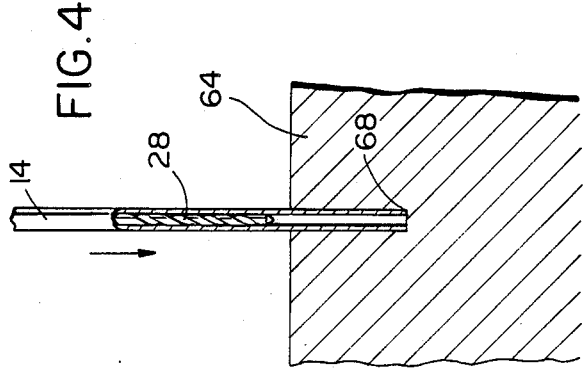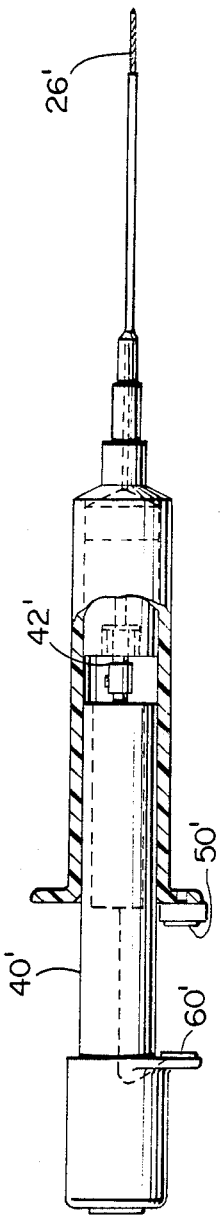

BIOPSY DEVICE

BACKGROUND OF THE INVENTION

1. Field of the Invention

This invention relates to a device for obtaining tissue samples from the body, and more particularly to a biopsy device which utilizes drilling and aspirating techniques to obtain samples for cytologic and histologic evaluation.

2. Description of Prior Art

When a physician is diagnosing a patient, it is often necessary to take tissue samples from the patient to determine a proper course of treatment. One commonly used method for obtaining tissue samples requires the use of a biopsy device. When choosing such a device, the physician, or medical technician who is using the device, must consider several criteria.

First, it is desirable to obtain a sufficient amount of tissue to enable an accurate analysis by a physician, such as a pathologist. Further, it is desirable for the device to be of simple construction and easy to operate. In addition, it is also desirable that the amount of trauma suffered by the patient as a result of the sampling procedure be minimized.

Several devices have been disclosed which are used to obtain tissue samples. In some of these devices, the technique used for obtaining samples involves either drilling or aspirating.

U.S. Pat. No. 3,749,085 to Wilson et al. discloses a vascular tissue removing device. The device is a scraping tool having a plurality of helically shaped wires of different lengths and provided with radially projecting chisel pointed tips. The tool is rotated to scrape extended areas of the end or side walls of the branch of the cavity which is to be examined.

U.S. Pat. No. 3,837,345 to Matar discloses a venous valve snipper. The device contains two parts, a tubular member and a distal head member. These members are connected so that the distal head may be longitudinally projected beyond the tubular member. Upon reaching the location of venous valves, the head is longitudinally projected beyond the tube so that the entire head passes through the valves. The head, which has on its interior two sharp cutting blades, is then retracted to cause to impale the valve leaflets on the blades, and to cause the head member to recombine with the tubular member. An annular cutting member on the tubular member snips off the valve leaflets.

U.S. Pat. No. 4,177,797 to Baylis et al. discloses a rotary biopsy device. The device includes a needle which is projected from a tube to initially puncture the skin of the patient's body. The needle is then rotated to facilitate penetration into the body tissue. The distal end of the needle has a helical cutting blade for capturing a sample and terminates in a conical needle point for initially puncturing the skin and penetrating the body tissue. The tube, which can also cut through the skin because it has sharp chisel pointed blades on its surface, is pushed downward through the skin over the already-inserted needle. The needle thus acts as a guide for the tube. The entire apparatus, including the sample trapped between the tube and needle, is thereafter withdrawn.

U.S. Pat. No. 4,542,749 to Caselgrandi et al. discloses a syringe for use in hypodermic biopsy, featuring an automatic plunger-return. The device disclosed in this patent is constructed of plastic, glass, or metal and includes a syringe accepting an ordinary hypodermic needle. A cylindrical body is provided with a central cylindrical cavity which is surrounded by an annular cavity. A plunger is located in the central cylindrical cavity in fluid/air-tight fashion and caused to slide. Use of the plunger according to the device draws a small quantity of organic tissue or fluid through the hypodermic needle as a result of the suction created between the plunger and the syringe chamber.

The devices described above serve many useful purposes in the medical field, yet none meets the need of a simplified, easy-to-operate biopsy device which utilizes both drilling and aspirating techniques to retrieve a significant amount of tissue within a short period of time. The present invention meets these above criteria and possesses the additional advantages of being easy to operate and subjecting the patient to only minimal trauma. Moreover, the device according to the present invention ma be utilized to retrieve tissue samples from substantially all regions of the body.

SUMMARY OF THE INVENTION

The present invention relates to a biopsy device for retrieving biopsy samples from various regions of the body, which utilizes both drilling and aspirating techniques. The device contains three basic components. The first component is a syringe housing having a hollow cannula coupled to it at its distal end. Located inside the syringe is the second component, a rotatable drill bit and a plunger, such that when the plunger is in contact with the distal interior end of the syringe housing, the drill bit extends through the distal tip of the syringe and through the cannula such that the tip of the drill bit protrudes a short distance beyond the distal tip of the cannula. The drill bit/plunger component is designed to undergo rotational motion. To provide such rotational motion, the third component, a rotational energy element, whose distal portion also fits within the interior of the syringe housing, is coupled to the drill bit/plunger component. Once the rotational energy element has been coupled to the drill bit/plunger component, the rotational energy element may be actuated to impart rotational motion to the drill bit.

To obtain a biopsy tissue sample, a standard two-piece biopsy needle having a stylet and cannula is introduced into the biopsy site. The stylet, which prevents unwanted tissue from entering the cannula, is then removed. The syringe housing component, having the drill bit/plunger component contained therein, is then connected to the cannula by coupling the proximal end of the cannula to the external distal potion of the syringe housing. The rotational energy element is then inserted into the syringe housing and is coupled to the drill bit/plunger component so that rotational motion produced by the rotational energy device can be imparted to the drill bit.

The rotational energy device is then actuated to cause the drill bit to rotate, and the device tissue sample to accumulate. This accumulation takes a very short amount of time, typically ranging from about 1 to 10 seconds. Thereafter, while the rotational energy element is still coupled to the drill bit/plunger component, the rotational energy element, and in turn the drill bit/plunger component, is translated from the housing's distal end to the housing's proximal end, yet remains inside the housing. Therefore, the tissue sample is drawn into the cannula by utilization of the suction forces created between the plunger and the syringe housing. The entire biopsy device is thereafter withdrawn from the patient, while maintaining full aspiration.

The biopsy specimen is then propelled from within the syringe housing through the cannula by exerting longitudinal pressure on the rotational energy element so that the plunger moves forward and abuts the distal end of the syringe housing. Once the specimen has been propelled out of the syringe housing, the rotational energy device is disengaged from the remainder of the device, and the syringe housing and drill bit/plunger component are discarded.

Thus, it is an object of the present invention to provide a biopsy device which can easily and reliably obtain biopsy samples by utilizing drilling and aspirating techniques.

Another object of the present invention is to provide a biopsy device having a minimal number of components which enables simplified use.

It is a further object of the present invention to utilize familiar-sized and -shaped housings to construct the device, so that medical personnel are familiar with the look and feel of the device components.

A further object of the present invention is to provide a device wherein a minimal number of components are used, and wherein some of the components are disposed of after use.

It is an additional object of the present invention to provide a biopsy device which causes a minimal amount of trauma to the patient sampled.

It is a further object of the present invention to utilize rotational energy to power to device while operating at slow speeds, from approximately 60 to 800 revolutions per minute.

It is an additional object of the present invention to utilize conventional fittings to construct the biopsy device.

It is further object of the present invention to use a rotational energy device which may be recharged after use.

It is an additional object of the present invention to provide a biopsy device which is battery-powered and wherein the electrical connection of the battery to a rotational energy device occurs at the outer surface of the device housing.

These and other objects of the present invention will become clear when reference is made to the accompanying drawings taken in conjunction with the following description.

BRIEF DESCRIPTION OF THE DRAWINGS

FIG. 1 is a perspective view of a biopsy device embodying the teachings of the instant invention.

FIG. 2 is an exploded view of the device of FIG. 1.

FIG. 3 is a view taken along line 3—3 of FIG. 1.

FIG. 4 is a view of the biopsy device of FIG. 1 entering an organ from which a sample is to be obtained after the wall of the organ has been punctured by a biopsy needle.

FIG. 5 is a view of the biopsy device collecting a tissue sample from the organ shown in FIG. 4

FIG. 6 is a view of the biopsy device according to FIG. 1 showing the drill bit/plunger component having obtained a tissue sample while being retracted within the syringe housing.

FIG. 7 is a view showing the description of the biopsy sample obtained from the patient of FIG. 4 into a petri dish.

FIG. 10 is an alternate embodiment of a biopsy device embodying the teachings of the instant invention.

Detailed Description of the Drawings

Figure 8:
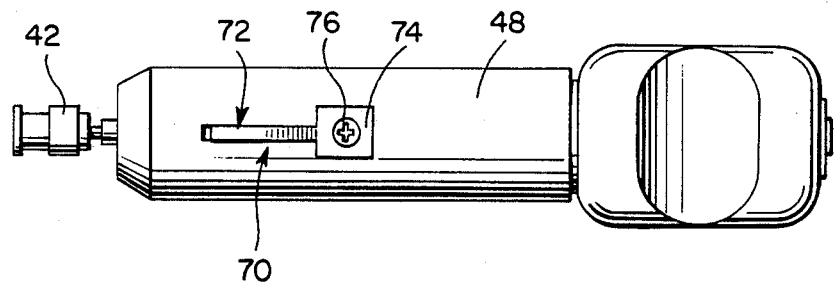
FIG. 8 is a plan view of a rotational energy element with an aspiration lock.

In describing the invention illustrated in the drawings, specific terminology will be resorted to for the sake of clarity. However, the invention is not intended to be limited to the specific terms so selected; rather, each specific term includes all technical equivalents which operate in a similar manner to accomplish a similar purpose.

Referring now to the drawings, and more particularly FIGS. 1 and 2, the biopsy device is designated as 10. Device 10 includes a syringe housing 12, which may be a typical 20cc disposable plastic syringe housing. A proximal end 16 of a cannula 14 is coupled via coupling 18 and inwardly threaded LUER-LOK fitting 20 to syringe housing 12. Located at the proximal end of housing 12 is finger holder 22. The most distal portion of housing 12 is open or hollow.

Mounted inside housing 12 is rotatable drill bit/plunger component 24. Drill bit/plunger component 24 includes drill bit 26 having cutting tip 28 located at is distal tip. The cutting blade 30 of tip 28 is helically shaped. Drill bit 26 is preferably made of standard gauge, medical grade materials.

Drill bit 26 passes through the center of plunger 32 at its proximal end and into connector 34. Connector 34 has on its internal surface inward threads 36 and cylindrical connection pin 38, as shown in FIG. 3.

Also shown in FIGS. 1 and 2 is rotational energy element 40. Rotational energy element 40 is connected to drill bit/plunger component 24 at its distal end by rotatable coupling 42. Coupling 42 engages with threads 36 and connection pin 38 of drill bit/Plunger component 24. The precise connection of rotational energy element 40 to drill bit/plunger component 24 will be described later with respect to FIG. 3.

Referring to FIG. 3, rotational energy element 40 is shown in greater detail. The proximal end of element 40 contains recessed on/off button switch 44. Casing 48 surrounds the power and drive mechanism of the rotational energy element. One terminal of switch 44 is connected to a terminal of battery 50. The other terminal of battery 5 is connected to one terminal of a low-voltage mini-motor 51. The other terminal of the mini-motor 51 is connected to the other terminal of switch 44 so as to complete a circuit. The motor 51 is equipped with a motor shaft 54 which extends beyond casing 48. Coupling 42 is held onto motor shaft 54 by any suitable fastener, such as set screw 58.

In FIG. 3, the connection of rotational energy element 40 to drill bit/plunger component 24 is shown in detail. Coupling 42, which is mounted onto motor shaft 54 of rotational energy element 40, has outwardly extending tabs 60. Outwardly extending tabs 60 align with threads 36 of connector 34. Coupling 42 also has longitudinal channel 62, which is sized to surround connection pin 38 when element 40 is coupled with component 24.

To form the connection between element 40 and component 24, opening 62 is placed over connection pin 38. Thereafter, coupling 42 is rotated one-half turn clockwise so that tabs 60 engage with inward threads 36. This type of engagement is commonly known in the medical profession as a LUER-LOK fitting.

Having described the preferred embodiment of the biopsy device, the use of device 10 will be described with reference to retrieving a biopsy sample from an organ, as is best shown in FIGS. 4 through 7.

To obtain a biopsy sample, an ordinary biopsy needle having a stylet (not pictured) and cannula is utilized. The stylet portion of the needle is used to puncture the skin or wall of the organ to create a passageway through the subcutaneous tissue to the appropriate depth, bordering the region of the desired biopsy site. The entire needle is then inserted into the organ until it reaches a desired depth where a biopsy sample can be obtained. The exterior of the cannula may have 1 cm gradations to aid in the insertion to an appropriate depth. Thereafter, the stylet portion of the biopsy needle is withdrawn and discarded, leaving cannula 14, having coupling 18 located at its proximal end outside of organ 64, for coupling with syringe housing 12.

Syringe housing 12 initially includes plunger 32 of plunger/drill bit component 24 with a significant distal portion of drill bit 26 extending through and beyond the open distal tip of housing 12. Housing 12 is thereafter coupled to cannula 14 by advancing drill bit 26 through coupling 18 until coupling 18 abuts hollow inwardly threaded LUER-LOK fitting 20 of housing 12. Thereafter, coupling 18 is rotated one-half turn clockwise so that its upwardly extending tabs 21 mate with inward threads of fitting 20 (not pictured). At this position, the terminal tip of the drill bit extends distally beyond the distal tip of the cannula.

When in this position, plunger 32 abuts the distal end 66 of housing 12, and tip 28 of drill bit 26 extends longitudinally beyond the distal end 68 of cannula 14. The diameter of plunger 32 is larger than the diameter of fitting 20 so that plunger 32 does not pass through fitting 20, but rather abuts end 66 and seals off the open end of housing 12.

Rotational energy element 40 is thereafter coupled with drill bit/plunger component 24 by inserting element 40 into housing 12 and interconnecting the LUER-LOK fitting of coupling 42 to drill bit/plunger component 24, as described above with reference to FIG. 3. Once the three basic components of the biopsy device have been connected, the device may be used to capture a sample.

Referring to FIG. 5, on/off switch 44 is depressed to impart rotational motion to motor shaft 54, coupling 42 and, in turn, connector 34. This causes tip 28 to rotate and thereby causes a tissue sample 70 to be cut and to accumulate onto the blade 30 of spinning tip 28. On/off switch 44 is depressed to the on position for a sufficient time to enable tip 28 to capture a sufficient amount of biopsy sample 70. This typically takes between about 2 to 4 seconds.

Referring to FIG. 6, once enough tissue sample has accumulated on tip 28, rotational energy element 40 and the proximal end of drill bit/plunger component 24 is longitudinally displaced in a direction out of the proximal end of syringe housing 12. This is done by exerting longitudinal force in the proximal direction to casing 48 of element 40. This causes connector 34 and plunger 32 to be longitudinally displaced in the interior of syringe housing 12. This further causes tip 28 of drill bit 26 to be withdrawn inside cannula 14. Further, the movement of plunger 32 towards the proximal end of housing 12 creates suction or aspirating action through cannula 14. The tissue sample 70 is thereby withdrawn through cannula 14 a distance away from distal tip 68. Along with the captured tissue sample, liquid or other matter at the biopsy site is withdrawn into the cannula and thus into the syringe housing by the suction force created by withdrawal of the plunger. Alternately, suction or aspirating action can be performed by a separate aspiration device, which produces a suction force at the biopsy site.

Figure 9:
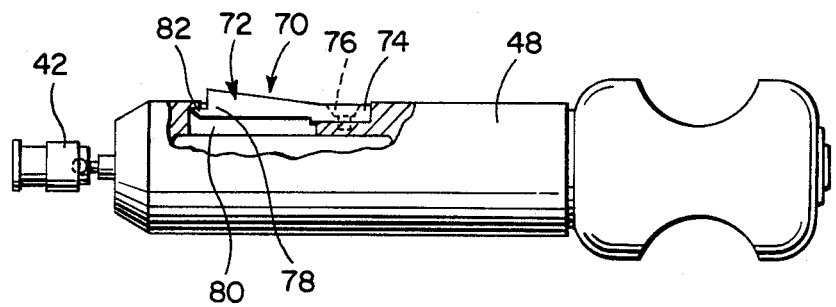
FIG. 9 is a side, partial sectional view of FIG. 8.

While element 40 is being longitudinally displaced in a proximal direction through the interior of housing 12, on/off switch 44 should be depressed in an on position until approximately one inch of the proximal portion of drill bit 26 has been drawn into housing 12. Thereafter, on/off switch 44 is deactuated, terminating the rotational energy supplied by element 40. Element 40 and component 24 are longitudinally displaced an additional proximal distance through the interior of housing 12 by applying longitudinal forces to casing 48 in a proximal direction until an aspiration lock 70, shown in FIGS. 8 and 9, is withdrawn past the finger holder 22 at the proximal end of housing 12. When withdrawn from the housing, biased projection 72 is released to extend above the surface of the casing 48. One end 74 of the projection 72 is secured to the casing 48 by screw 76. The other end 78 of the projection moves within recess 80, and tip 82 engages casing wall 84 to limit the extent of projection of the projection above the casing.

During aspiration of the tissue, as the plunger 32 moves proximally and the syringe fills with fluid, there is a tendency for the plunger 32 to move distally upon release of tension. This would cause an injection of the aspirated fluid ("seeding"), possibly at a location different from the site from which the fluid was withdrawn. Such an occurrence potentially spreads whatever disease was located at the biopsy site. Therefore, the aspiration lock is released when the casing 48 has been withdrawn beyond the proximal end of the syringe. The release of projection 72 above the casing 48 notifies the operator that the plunger 32 has been withdrawn a sufficient distance and that it is possible to release tension on the plunger without transmittal of aspirated fluid to a new tissue location.

Referring to FIG. 7, the solid and liquid biopsy sample is deposited into petri dish 72, by exerting longitudinal pressure on element 40 and thereby causing drill bit/plunger component 24 to move longitudinally inside housing 12 towards distal end 66. When plunger 32 abuts distal end 66, the biopsy sample 70 will have advanced through cannula 14 and is deposited in petri dish 72.

After biopsy sample 70 has been deposited in petri dish 72, and while element 40 is still coupled to component 24, the user again retracts element 40 and plunger/drill bit component 24 by exerting longitudinal pressure on element 40 in a proximal direction. Once coupling 42 is longitudinally extended beyond holder 22, the user rotates coupling 42 one-half turn counterclockwise to disengage element 40 from component 24. Element 40 may be recharged for future use, and housing 12 and component 24 are discarded.

In the preferred embodiment of the biopsy device, housing 12 is typically a 20 milliliter syringe housing. However, other sized housings are envisioned as being within the scope of this invention. Housing 12 is made of clear plastic. However, other materials for housing 12 may be used within the scope of this invention. Cannula 14 is of a gauge normally used for biopsy needles.

In the preferred embodiment of the biopsy device, drill bit 26 is made of stainless steel and surrounding cannula 14 is also made of stainless steel. Other materials may be used for the drill bit and cannula, such as non-magnetic materials. When plunger 32 abuts distal end 66, cutting tip 28 projects about 1.5 centimeters distally fro distal tip 68 of cannula 14. However, it is envisioned within the scope of the invention that other lengths of projection may be utilized, with the proviso that at least a portion of the drill bit must extend beyond the distal tip of the cannula.

Motor shaft 54 preferably operates between about 200 and about 800 revolutions per minute. A higher speed may be envisioned but is not considered necessary to the success of the invention.

Element 40 is preferably coupled to component 24 by a LUER-LOK type fitting. However, it is envisioned that other types of connectors may be used, with the proviso that the connection must be such that drill bit/plunger component 24 rotates upon rotation of rotational energy element 40.

Rotational energy element 40 is a hand-held, battery-powered motor which may be recharged after use. Other means of powering the motor to cause the motor shaft to rotate may be practiced within the scope of this invention. For example, FIG. 8 illustrates an alternative means for powering the biopsy device embodying the teachings of the present invention. The device shown in FIG. 10 is nearly identical to the device shown in FIG. 1, with the exception of the electrical means used to impart rotational energy to rotational energy element 40'.

As seen in FIG. 10, rotational energy element 40' is powered by battery 50', which is mounted on the external surface of holder 22', near its proximal end. To create an electrical contact, the proximal portion of element 40' has terminal 60', which, when in contact with battery 50', imparts rotational motion to element 40' and, in turn, coupling 42' and drill bit 26'. By using this arrangement, battery 50' is external to casing 48' and may thereby be easily replaced.

In addition to the embodiments shown in FIGS. 1 and 10, other mounting arrangements for the battery are envisioned within the scope of the invention.

Thus, by using the above-described biopsy device, tissue samples can be efficiently retrieved using a minimal amount of effort. The operation of the device is simple and causes the patient a minimal amount of trauma.

From the above, it should be apparent that many modifications and variations of the present invention are possible. It is, therefore, to be understood that within the scope of the appended claims, the invention may be practiced otherwise than as specifically described.

What is claimed is:

1. A device for obtaining biopsy samples, said device comprising:
 a housing having proximal and distal ends and a distal tip terminating the distal end, a cannula having proximal and distal ends mounted at the distal end of said housing, the distal tip of said housing being open;
 a drill bit/plunger component slidably mounted in said housing, said drill bit/plunger component including a plunger and a drill bit having proximal and distal ends with a cutting tip at the distal end of said drill bit, said drill bit extending through said plunger in a fluid-tight seal, said drill bit/plunger component being sized to fit within said housing such that when said drill bit/plunger component is inserted in said housing, said drill bit passes through said cannula and such that when said plunger abuts the distal end of said housing, said cutting tip extends beyond the distal end of said cannula,
 a rotational energy element for providing rotational energy to said drill bit/plunger component,
 coupling means for coupling said rotational energy element to said drill bit/plunger component, and
 means for actuating said rotational energy element so as to impart rotational movement to said coupling means and said component.

2. The device according to claim 1, wherein said housing is a syringe housing.

3. The device according to claim 2, wherein said housing is made of glass.

4. The device according to claim 1, wherein said rotational energy element includes motor means for generating said rotational energy and switch means connected to said motor means for actuating said motor means.

5. The device according to claim 1, wherein said rotational energy element includes means to drive said rotatable coupling so that said coupling and said cutting tip rotate at a rate between 60 to about 800 revolutions per minute.

6. The device according to claim 1, wherein said means for actuating said rotational energy element comprises a battery mounted on an external portion of said rotational energy element and a contact mounted on an external portion of the proximal end of said housing such that when said battery contacts said contact, rotational energy is imparted to said rotational energy element.

7. The device according to claim 1, wherein said cutting tip includes a blade which is helically shaped.

8. The device according to claim 1, wherein said coupling means which couples said rotational energy element to said drill bit/plunger component comprises an opening with threads, and wherein said rotational energy element comprises a pin with laterally extending tabs so that said pin is inserted into said opening and rotated one-half turn relative to said opening for engaging said laterally extending tabs into said threads.

9. The device according to claim 1, wherein said housing is made of clear plastic.

10. The device according to claim 1, wherein said cannula and said drill bit are made of medical grade stainless steel materials.

11. A method for obtaining a biopsy tissue sample, said method comprising the steps of:
 puncturing said tissue to effect a passageway for a biopsy device while inserting a hollow cannula,
 providing a device having a housing with an open distal tip and a drill bit/plunger component including a plunger and a drill bit having a cutting tip, said drill bit extending through said plunger, said component being located in said housing such that a distal portion of said drill bit extends through said open distal tip and said plunger abuts the distal tip, said plunger having a diameter greater than the diameter of said distal tip,
 coupling the proximal end of said cannula to the open distal tip of said hosing such that said cutting tip passes through and extends beyond the distal end of said cannula, providing a rotational energy element capable of producing rotational energy, coupling said rotational energy element to said drill bit/plunger component by means of a rotatable coupling, actuating said rotational energy element to cause said coupling and said drill bit to rotate, collecting a biopsy tissue sample on said cutting tip, aspirating said sample into said cannula by retracting said rotational energy element and said drill bit/plunger component in a proximal direction, withdrawing said cannula and drill bit from the tissue, and depositing said biopsy sample by exerting pressure on said rotational energy element and, in turn, said drill bit/plunger component in a distal direction.

12. The method according to claim 11, further comprising the step of detaching said rotational energy element from said drill bit/plunger component and disposing of said housing and drill bit/plunger component.

13. The method according to claim 11, wherein said step of actuating said rotational energy element further comprises actuating a motor powered by a battery by switching an on/off switch means connected to said battery for actuating said motor.

14. The method according to claim 11, wherein said rotational energy element delivers rotational energy to said rotatable coupling so that said coupling and said cutting tip rotate at a rate between about 60 and about 800 revolutions per minute.

15. The method according to claim 11, further comprising the step of maintaining rotational movement of said rotational energy element while aspirating said sample.

16. The method according to claim 11, wherein said step of coupling said cannula to said housing further comprises coupling said cannula to said housing by a first coupling means and wherein said step of coupling said rotational energy element to said drill bit/plunger comprises coupling said rotational energy element to said drill bit/plunger component by a second coupling means.

17. The method according to claim 11, wherein said collecting step takes between 1 and about 10 seconds.

18. A biopsy device comprising:

a syringe housing having an open distal end, a cannula mounted on said distal end of said housing, coupling means slidably mounted in said housing for transmitting a rotational drive force, said coupling means including a plunger and drill means extending distally through said plunger, said open distal end of said housing and said cannula for collecting a biopsy sample, and drive means connected to said coupling means for rotating said coupling means to collect a biopsy sample when said plunger is slid in a distal direction to project said drill bit beyond a distal end of said cannula and cut tissue from a biopsy site.

19. A biopsy device as in claim 18, wherein said drive means is slidably mounted in said housing.

20. A biopsy device as in claim 19, wherein said drive means includes a connector threadingly engaging said coupling means for moving said coupling means when said drive means is moved within said housing.

21. A method of obtaining a biopsy sample from tissue, said method comprising:

puncturing tissue with a stylet and cannula at a biopsy site from which a biopsy sample is to be taken, inserting a rotating drill means through said cannula to extend from a distal end of said cannula for rotating a drill bit to collect a biopsy sample, and withdrawing said rotating drill means from said biopsy site while aspirating said biopsy site.

22. A method of obtaining a biopsy sample as in claim 21, wherein during aspiration of the biopsy site, liquid is withdrawn into a syringe housing.

23. A method of obtaining a biopsy sample as in claim 22, and further comprising the step of mounting said drill means on a coupling which is rotatably mounted in said housing.

24. A method of obtaining a biopsy sample as in claim 21, wherein the puncturing of the tissue is done with a biopsy needle which includes said stylet and said cannula.

25. A method of obtaining a biopsy sample as in claim 21, wherein said drill means includes cutting means for collecting the biopsy sample.

* * * * *